United States Patent [19]

Guis

[11] Patent Number: 5,114,339

[45] Date of Patent: May 19, 1992

[54] METHOD OF APPLYING AN ORTHODONTIC AID, AND MOLD THEREFOR

[75] Inventor: Marinus B. Guis, Sliedrecht, Netherlands

[73] Assignee: Orthodontie Research B.V., Sliedrecht, Netherlands

[21] Appl. No.: 663,366

[22] Filed: Mar. 1, 1991

[30] Foreign Application Priority Data

Dec. 18, 1990 [NL] Netherlands .................. 9002792

[51] Int. Cl.$^5$ ................................ A61C 3/00
[52] U.S. Cl. .................................... 433/24; 433/3
[58] Field of Search ........................... 433/24, 3

[56] References Cited

U.S. PATENT DOCUMENTS

| | | | |
|---|---|---|---|
| 3,738,005 | 6/1973 | Cohen et al. | 433/24 |
| 3,949,477 | 4/1976 | Cohen et al. | 433/24 |
| 4,516,938 | 5/1985 | Hall | 433/215 |
| 4,526,540 | 7/1985 | Dellinger | 433/24 |
| 4,609,349 | 9/1986 | Cain | 433/6 |
| 4,932,866 | 6/1990 | Guis | 433/24 |

Primary Examiner—John J. Wilson
Attorney, Agent, or Firm—Peter L. Michaelson

[57] ABSTRACT

The invention relates to a method of applying an orthodontic aid to at least one tooth in a row of teeth. A cast of the row of teeth is made by means of molding and counter-molding. The aid is temporarily secured to the cast in the desired position. A deformable layer of material is applied to the cast with aid, and this layer is deformed to conform to the shape of the cast with aid and thus a mold is formed. The mold with aid is positioned on the row of teeth and the bonding agent applied for securing the aid is allowed to harden in a controlled manner. Then the mold is removed, and the aid remains behind, secured to the row of teeth by means of the bonding agent. According to the invention prior to placing the mold with the aid on the row of teeth, an adhesive layer is applied to at least a part of the surface of the mold, that is brought into contact with the row of teeth. This adhesive layer has weaker adhesive strength than the bonding agent for securing the aid to the row of teeth. When the mold is placed on the row of teeth, it is temporarily retained in that position by means of the adhesive layer. The invention further relates to a mold with an adhesive layer for use in this method.

18 Claims, 2 Drawing Sheets

METHOD OF APPLYING AN ORTHODONTIC AID, AND MOLD THEREFOR

BACKGROUND OF THE INVENTION

This invention relates to a method of applying an orthodontic aid to at least one tooth in a row of teeth, comprising making a cast of said row of teeth by means of molding and counter-molding;

temporarily securing the aid to the cast in the desired position;

applying a deformable layer of material to the cast with aid, and deforming said layer to conform to the shape of the cast with aid to form a mold;

placing the mold with aid on said row of teeth, the bonding agent for securing the aid being permitted to harden in a controlled manner, followed by removing the mold, leaving the aid affixed to the row of teeth by means of the bonding agent.

Such a method is known from U.S. Pat. No. 3,738,005. When that method is used, the operations in the patient's mouth can be reduced to a minimum, while at the same time the use of a mold enables optimum positioning of the aid.

Is has been found that it is of great importance that the mold does not shift or otherwise move during the hardening of the bonding agent. Although the mold, due to its shape being adapted to the row of teeth, already takes care of a proper positioning and retention, movements by the patient and the person who is treating the patient can cause of the mold during the hardening which might adversely affect the bonding of the bonding agent to the row of teeth.

SUMMARY OF THE INVENTION

It is an object of the invention to improve a method of the type described hereinabove in such a way that the problem discussed can be overcome.

This is achieved in accordance with the invention, when prior to placing the mold with aid on the row of teeth, an adhesive layer is applied to at least a part of the surface of the mold, that is brought into contact with the row of teeth, which adhesive layer has weaker adhesive strength than the bonding agent for securing the aid to the row of teeth, and the mold, when placed on the row of teeth, is temporarily retained in that position by means of the adhesive layer.

Owing to these steps, the mold, upon being placed on the row of teeth, is retained in position by means of the adhesive layer in such a way that the mold can be released, so that the risk is eliminated of any errors occurring due to the fact that the mold must be retained during hardening of the bonding agent. An additional advantage is that the mold can remain in position longer without this causing any inconvenience to the patient or the person who is treating the patient, which, in turn, can promote optimum hardening of the bonding agent.

The adhesive layer can be applied after forming the mold and prior to positioning on the row of teeth, for instance by means of a "spray" method or by applying it with a brush. When the adhesive layer is not applied immediately prior to the positioning of the mold on the row of teeth, provisions will have to be made for preventing any undesirable matter from adhering to the adhesive layer. Applying the adhesive layer immediately prior to positioning will be done by the person who is treating the patient, which can delay the treatment. Accordingly, it may be preferable for the adhesive layer to be applied when the mold is made. In such cases it is preferable, and in accordance with a further elaboration of the invention, that a support is provided on the adhesive layer, which support can be removed leaving the adhesive layer on the deformable layer of material, the adhesive layer and the support being provided on the deformable layer prior to deforming the deformable layer of material over the cast to form a mold, the deformable layer of material is deformed with the support turned towards the cast, the support, after the mold has been removed from the cast, is locally cut away or cut through in correspondence with the configuration of the aid, and the support is pulled from the adhesive layer prior to positioning the mold on the row of teeth.

By virtue of these steps, an adhesive layer is provided without this layer rendering the making and finishing of the mold difficult owing to its adhesive properties or running the risk of being contaminated by undesirable matter. Such an adhesive layer can, as it were, be provided automatically by choosing as a starting material for the making of the mold a deformable material with an adhesive layer and a support provided thereon.

When the deformable layer is being deformed on the cast, the aid, when pressing into that layer, will also deform the adhesive layer and the support. The aid is disposed on the other side of the support than the deformable layer of material. Removing the support, therefore, would also amount to pulling the aid from the mold. This explains why the support is locally cut away or cut through.

When the aid consists of a plurality of brackets to be mutually independently fixed to a tooth, the aid can be most readily prevented from being removed from the mold when the support is being pulled off, when, in accordance with a further embodiment of the invention, the support is cut through and around the brackets, whereby a number of portions of the support are cut loose. When the support is pulled off, such portions of the support as have been cut loose, and hence the aid, retain their position.

The surface of the adhesive layer from which the support has been removed will generally be large enough for the desired temporary bonding of the mold to the row of teeth to be accomplished. However, when a maximum adhesive surface is desirable during positioning on the row of teeth, it is preferable, and in accordance with a further embodiment of the invention, that after removing the mold from the cast, the brackets are temporarily removed from the mold, such portions of the support as have been cut loose are pulled from the mold and the brackets are re-positioned in the mold.

When the aid to be positioned on the row of teeth is a wire, the aid can be prevented from being removed from the mold during pulling off of the support in the simplest manner when, in accordance with a further embodiment of the invention, the wire is temporarily removed from the mold after the latter has been removed from the cast, the support is cut through in correspondence with the impression which the wire has left in the mold with adhesive layer and support, the mold is provided with a perforation at each location where the wire is to be secured to the row of teeth, the shape and dimensions of this perforation determining the configuration of the point of attachment and said perforation having an open end on the side of the mold that does not come into contact with the row of teeth, and the wire is then re-positioned in the mold through the cut in the support.

By virtue of these steps, the wire can be secured to the row of teeth in such a way that the bonding agent in hardened condition has a predetermined shape and dimensions, as known from EU-A-0 303 327 or U.S. Pat. No. 4,932,866 corresponding thereto, but the present invention provides an additional guarantee as regards the undisturbed hardening of the bonding agent. By virtue of the fact that the wire is a relatively thin, elongated member, making a cut in the support will suffice. It will be clear it is also possible to cut through the support around the wire, which, however, is less effective in this case, since the wire must be removed from the mold anyway for the perforations to be provided.

Thus, securing the mold with wire and perforations by means of an adhesive layer may have further advantageous effects for the method as a whole and the results thereof. Indeed, in accordance with a further embodiment of the invention, the temporary securement referred to offers the possibility of providing the bonding agent, via the open end of a perforation, after positioning the mold on the row of teeth and temporarily securing it by means of the adhesive layer. By virtue of the fact that the edge of a perforation of the mold abuts a tooth on the side of the row of teeth in complete surface-to-surface securement, an accurately defined hollow is obtained, which can be optimally filled with bonding agent, partly because the temporarily secured mold enables full concentration on the filling thereof.

In order to favorably influence the filling of a perforation after the temporary securement of the mold to the row of teeth, it may be preferable and in accordance with a further embodiment of the invention, that starting from the side of the mold where the open end is disposed, at a comparatively short distance therefrom, a channel is provided that terminates in the perforation. On the one hand, these steps offer a separate possibility of escape for the air forced from the perforation by the bonding agent, while this channel may also serve as a kind of "gauge" as a means of indicating when the perforation is completely filled. On the other hand, such a channel may serve as an injection channel for the bonding agent, for example, when the perforation disallows ready access owing to anatomical proportions. In that case, the perforation may serve as an opening for discharging displaced air and as a means of indicating the degree of filling.

When the mold is to be removed after hardening of the bonding agent, it must be possible for the bonding agent hardened in the channel to be removed together with the mold. In order to initiate for this purpose a point of fracture at the point where channel and perforation meet, in accordance with a further embodiment of the invention, the channel may be of frustoconical configuration, the narrowest passage of said channel being disposed at the termination in the perforation.

As noted in the foregoing, the mold may also be provided with an adhesive layer but without a support. The adhesive layer may then be provided using auxiliary means which may or may not be covered or removed. In the manner described hereinabove, the mold may be provided with perforations which may or may not have a channel terminating in them. In the case of a non-covered adhesive layer, it will generally be preferable not to apply the adhesive layer until immediately prior to positioning the mold on the row of teeth, although earlier application is also possible, for example in the case of dust- and/or air-tight packing of the mold.

BRIEF DESCRIPTION OF THE DRAWINGS

The method of applying an orthodontic aid according to the invention will now be further explained and illustrated, with reference to the embodiments shown in the drawings, in which.

DETAILED DESCRIPTION

Figure 1:
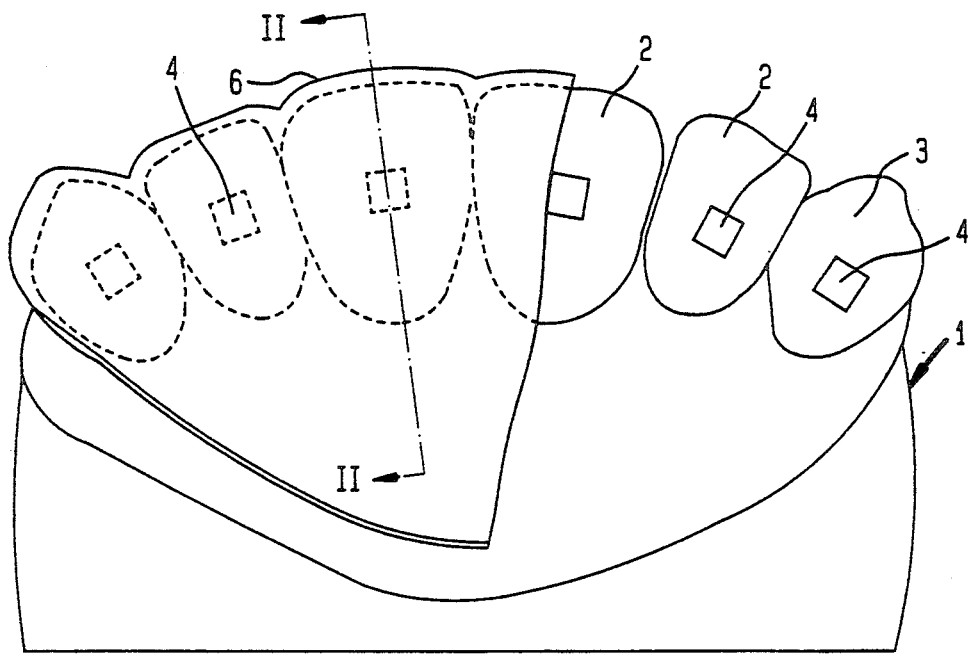
FIG. 1 is an elevational view of the inside of a cast of a row of teeth with a conformably shaped and partially cutaway mold with an orthodontic aid in the form of a plurality of brackets.
Figure 2:
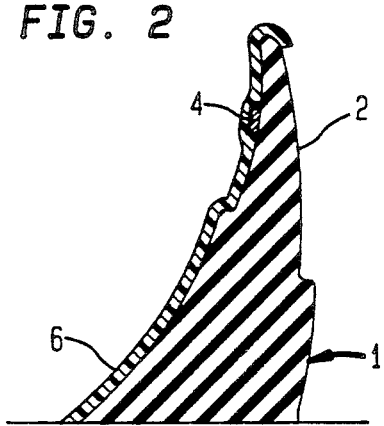
FIG. 2 is a sectional view taken on the line II—II of FIG. 1.

FIG. 1 shows a cast 1 of a row of teeth, comprising four incisors 2 and two eye-teeth 3, which cast has been obtained in the conventional manner by molding and counter-molding. An orthodontic aid in the form of a plurality of brackets 4 has temporarily been secured to the row of teeth 2, 3. Applied over the cast 1 with brackets 4, thus obtained, is a stretch of layered material which is composed of a layer 6a of permanently resilient material, an adhesive layer 6b and a support 6c, as shown in the cross-sectional view according to FIG. 3. The materials have been chosen such that upon pulling off the support 6c, the adhesive layer 6b remains behind on the layer 6a. The stretch of layered material is applied to cast 1 with the support 6c turned towards said cast 1, after which the layered material is deformed in a manner suitable for this material, for example by means of vacuum suction and/or a heat treatment, in such a way that a mold 6 is obtained which closely conforms to the cast 1 with brackets 4, with the brackets 4 being embedded in the mold 6, as shown in FIG. 2.

After deforming, the mold 6 with embedded brackets 4 is withdrawn from the cast, after which the support 6c is cut through around each embedded bracket 4.

Figure 4:
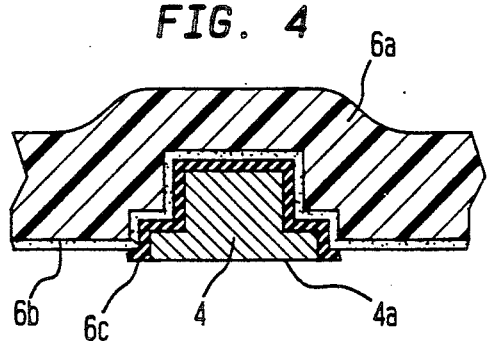
FIG. 4 is an enlarged, cross-sectional view of a part of the mold with an embedded bracket, according to FIG. 1, ready to be secured to a row of teeth.

Prior to positioning the mold 6 in the patient's mouth, the support 6c is removed, whereby the adhesive layer 6b is exposed. By cutting through the support 6c around each bracket 4, the portions of the support cut loose in this way will remain behind on the adhesive layer when the support 6c is pulled off the adhesive layer 6b. The portions referred to are disposed between the adhesive layer 6b and the brackets 4, so that the brackets 4, too, upon removal of the support 6c, will retain their position in the mold 6 and not be pulled from the mold together with the support 6c. A part of the cross-section of the mold then obtained is shown in FIG. 4. In this form—with bonding agent provided on the surface 4a of each bracket, that comes into contact with a tooth—the mold 6 is positioned on the row of teeth 2, 3 and pressed down, with the adhesive layer 6b taking care of a temporary securement of the mold to that row of teeth and maintaining a close surface-to-surface contact between the teeth and the surfaces 4a of the brackets 4, that are provided with bonding agent. In this fixated position of the mold 6, the brackets are disposed accurately in the position relative to the teeth, predetermined on the cast 1, in which position the brackets are secured to the teeth by the hardening of the bonding agent. Owing to the fact that after positioning and temporary securement, the mold can be released and need not be touched anymore, hardening of the bonding agent can take place reliably and without disturbance, whereby extremely reliable securement is obtained regarding both the desired position and the quality of the bond.

When it is considered desirable for the adhesive layer 6b bonding the mold 6 to a tooth 2, 3 to be in direct abutting contact with a bracket 4, i.e. independently of the manner in which the support 6c has been cut through around a bracket 4, it is also possible, after cutting, to pull the cut-loose parts of the support from the mold, removing the bracket along with it, and to subsequently re-position the bracket in its preformed recess. The bracket will then come into direct contact with the adhesive layer 6b and is completely surrounded by an exposed part of that adhesive layer, which upon removal of the remaining portion of the support 6c results in a maximum mold adhesive surface.

After sufficient hardening time of the bonding agent with which the bracket is secured to the tooth, the mold is removed by pulling off, with the brackets remaining behind on the teeth. It is observed that in virtue of the temporary securement of the mold, the hardening process will not be influenced by the inconvenience normally involved in retaining the mold motionlessly in the patient's mouth for some time, owing to the fact that such motionless retention has been made independent of both the patient and the person who is treating the patient.

Figure 3:
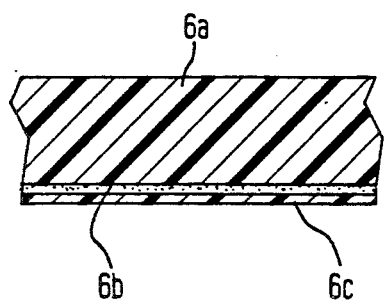
FIG. 3 is an enlarged cross-sectional view of a layered material for making a mold.
Figure 5:
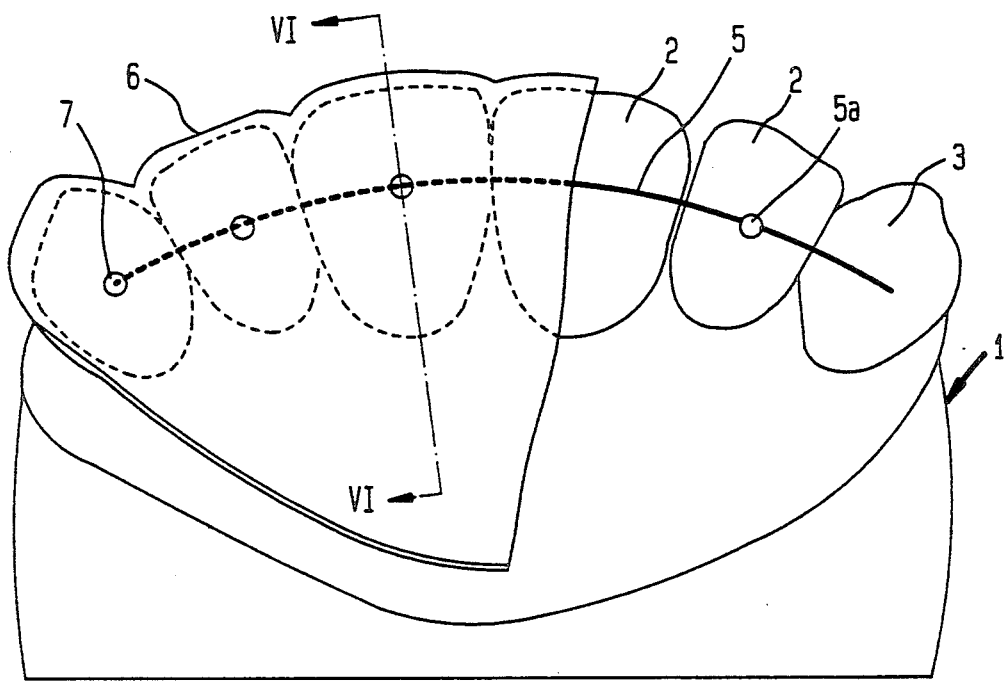
FIG. 5 is an elevational view of the inside of a cast of a row of teeth with a conformably shaped and partially cutaway mold with an orthodontic aid in the form of a wire.

FIG. 5 shows a cast 1 similar to FIG. 1 of a row of teeth comprising four incisors 2 and two eye-teeth 3. An orthodontic aid in the form of a wire 5 is formed on the cast and deformed until the desired form relative to the inner contour of the row of teeth 2, 3 has been obtained. Subsequently, the wire 5 is temporarily secured to the row of teeth in the desired position using two wax drops 5a. Over the cast 1 with wire 5, obtained in this way, a similar stretch of layered material as shown in FIG. 3 and discussed hereinabove, is applied, i.e. a material composed of a layer 6a of permanently resilient material, an adhesive layer 6b and a support 6c. The stretch of layered material is applied to the cast 1 with the support 6c turned towards said cast 1, after which the layered material is deformed in an appropriate manner, for example by means of vacuum suction and/or a heat treatment, in such a way that a mold is obtained conformably enclosing the cast 1 with wire 5, the wire 5 being embedded in the mold 6.

Figure 6:
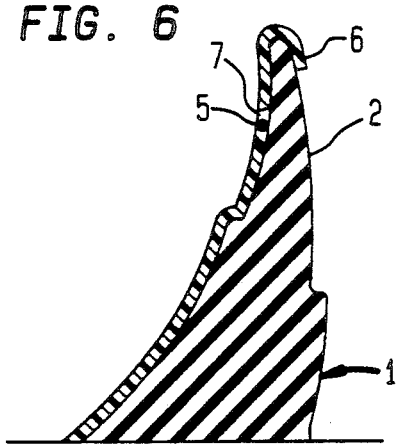
FIG. 6 is a sectional view taken on the line VI—VI of FIG. 5.
Figure 7:
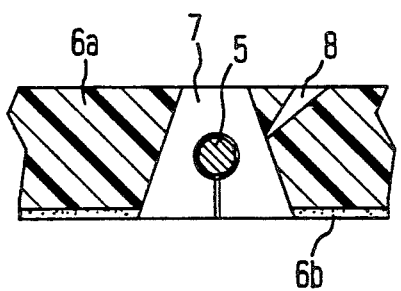
FIG. 7 is an enlarged, cross-sectional view of a part of the mold with embedded bracket, according to FIG. 5, ready to be secured to a row of teeth.

After deforming, the mold 6 with embedded wire 5 is removed from the cast and the wire 5 is withdrawn from the mold 6. At the locations where the wire is to be secured to the row of teeth, perforations 7 are provided in the mold, as shown in FIGS. 6 and 7, which perforations have the form and dimensions of the desired form and dimensions of the hardened bonding agent as contemplated. Since the mold 6 forms the counter-image of the row of teeth and the wire 5 to be secured thereto, the location of the points of attachment of the wire can be accurately determined.

After providing the perforations 7, an incision is provided in the support 6c, which makes it possible for the wire 5 to be pressed back into the mold beyond the support 6c and the adhesive layer 6b, with the wire 5 ending up entirely embedded in the layer 6a, not being pulled from the mold anymore when the support is removed. This makes the mold ready for the securement of the wire 5 to the row of teeth of the patient.

When an incision is made in the support 6c and the wire 5 is positioned in the mold 6 through that incision, the wire 5 will come into direct contact with the adhesive layer 6b. If this is considered undesirable or if there should be any other reasons, it is possible to cut loose the support 6c around the wire 5 after withdrawing mold 6 from cast 1, so that upon pulling off support 6c, the portion thereof that has been cut loose, will remain behind in a position where it surrounds the wire 5. This cutting operation can be done both before and after the provision of the perforations 7, preferably with the wire in position.

Securing the wire 5 to the row of teeth of the patient may be done as follows.

Prior to introducing the mold with embedded wire into the patient's mouth, first the support 6c is removed, whereby the adhesive layer 6b is exposed. The cross-section of this mold is shown in FIG. 7. Thus, the mold is positioned on the row of teeth and pressed down, with the adhesive layer 6b taking care of a temporary securement of the mold on the row of teeth and maintaining a close surface-to-surface contact between the teeth and the mold. Subsequently, the perforations 7 are completely filled with a bonding agent, which is introduced into the perforations from the open end of the perforations on the side remote from the plane of the teeth.

Depending on the filling instrument (not shown), filling of the perforations can be favorably influenced by providing a channel 8 at each perforation 7 as shown in FIG. 7, said channel extending from the perforation wall, conically widening towards the outer surface of the mold 6. During the filling of the perforation via its open end, air forced from the perforation can escape via the channel 8. When the perforation is completely filled, the bonding agent will escape via the channel 8, which provides a clear indication that the perforation is completely filled. Owing to the fact that the passage of channel 8 is relatively small compared with the passage of the perforation, complete filling of the perforation in a controlled manner can be accomplished with a minimum of additional bonding agent.

It will be appreciated the filling of the perforation 7 can also be done via the channel 8, which, to that effect, if so desired, may have any other configuration than that shown in FIG. 7. Filling via the channel 8 may be preferable when the location of the termination of the channel is more accessible than the termination of the perforation 7. Thus, in FIG. 6, the termination of a channel 8 extending in an upward direction will be more accessible to a filling instrument for the bonding agent than the termination of the perforation 7. When filling is done via the channel 8, displaced air can escape via the termination of the perforation 7, while any bonding agent forced from that termination will indicate when the perforation is filled completely.

The mold 6 temporarily secured to the row of teeth 5 does not only offer the advantage that it will remain in position in a reliable manner without requiring any operations to that effect, such as retention, to be performed, but also takes care that the edges of the perforations abut and continue to abut the adjacent tooth in optimum manner, so that a sharp adhesive boundary of the bonding agent is obtained. Moreover, the temporary securement of the mold offers the considerable advantage that during hardening of the bonding agent the mold need not be retained in position by hand, which considerably reduces the risk of bonding errors, for example as a result of undesirable and involuntary moving of the mold during the hardening of the bonding agent. A further advantage is that during the hardening process the mold can remain in position without any problems for a longer time than will be the case when it is pressed down and retained by hand. This, too, can favorably influence the securing process.

After the bonding agent has hardened sufficiently, the mold 6 can be removed by pulling it off the row of teeth, the resilience of the molding material permitting the wire 5 to remain behind without any problems. Any bonding agent hardened in the channel 8 will then, as a result of the conical configuration of the channel, break off substantially at the beginning at the perforation wall of the channel. Should this result in any small projections, they can readily and simply be removed by polishing.

It will be clear that within the framework of the invention many modifications and variants are possible. Thus, in the two embodiments discussed hereinabove, the assumption was that the orthodontic aid was to be positioned on the inside, the lingual or palatine side, of a row of teeth. Anyone skilled in the art will appreciate at once that the method can also be used with the same advantages and effects for positioning an orthodontic aid on the outside, the buccal side.

Further, in the discussion of the two embodiments, reference was made to a stretch of layered material comprising a layer of permanently resilient molding material. When the mold does not have any undercut parts, the layer referred to need not be resilient, but should be deformable only under certain conditions during modelling. This may for example be the case when working with brackets and a mold which does not curl over the top of the row of teeth in the manner shown in FIG. 2.

Although it is clearly preferred to start from a stretch of layered material provided with an adhesive layer and a support, the invention is explicitly understood not to be limited thereto. The same positioning and hardening advantages, as well as any filling advantages, can be obtained when the adhesive layer is not applied until after molding and optionally further treating the mold. The adhesive layer can be applied at any moment between the withdrawal from the cast and the positioning of the mold in the patient's mouth. When the adhesive layer is applied during or directly after the treatment of the mold, i.e. generally outside the doctor's treatment room, the exposed adhesive layer will be screened from the environment in some manner or other so as to prevent any dust or other matter from adhering. Such screening is comparable to the support 6c. When the adhesive layer is applied right before positioning on the row of teeth, such screening may clearly be omitted, although the adhesive itself will have been protected or screened up to the moment of application.

Further, it is also possible to fill the perforations, wholly or partly, with bonding agent, before the mold is introduced into the patient's mouth. Complete filling will generally be necessary when, instead of perforations, recesses that do not extend to the outer surface are provided in the mold. Both in the case of recesses and in the case of perforations, channels starting therefrom may or may not be provided, which, as noted, may have a conical or any other configuration.

What I claim is:

1. A method of applying an orthodontic aid to at least one tooth in a row of teeth, comprising making a cast of said row of teeth by means of molding and counter-molding;

temporarily securing the aid to the cast in a desired position;

applying a deformable layer of material to the cast with aid, and deforming said layer to conform to the shape of the cast with aid to form a mold; and placing the mold with aid on said row of teeth, a bonding agent for securing the aid being permitted to harden in a controlled manner, followed by removing the mold, leaving the aid affixed to the row of teeth by means of the bonding agent; characterized in that:

prior to placing the mold with aid on the row of teeth, an adhesive layer is applied to at least a part of the surface of the mold that is brought into contact with the row of teeth, which adhesive layer has weaker adhesive strength than the bonding agent for securing the aid to the row of teeth; and the mold, when placed on the row of teeth, is temporarily retained in position by means of the adhesive layer.

2. A method according to claim 1, characterized in that a support is provided on the adhesive layer, which support can be removed leaving the adhesive layer on the deformable layer of material, the adhesive layer and the support being provided on the deformable layer prior to deforming the deformable layer of material over the cast to form a mold, the deformable layer of material is deformed with the support turned towards the cast, the support, after the mold has been removed from the cast, is locally cut away or cut through in correspondence with the configuration of the aid, and the support is pulled from the adhesive layer prior to positioning the mold on the row of teeth.

3. A method according to claim 2, wherein the aid consists of a plurality of brackets to be mutually independently secured to a tooth, characterized in that the support is cut through around the brackets, whereby a plurality of portions of the support are cut loose.

4. A method according to claim 2, wherein the aid is a plurality of brackets to be mutually independently secured to a tooth, characterized in that after withdrawing the mold from the cast, the brackets are temporarily removed from the mold, the portions of the support that have been cut loose are pulled off the mold and the brackets are re-positioned in the mold.

5. A method according to claim 2, characterized in that the aid is a wire which is temporarily removed from the mold after said mold has been removed from the cast, the support is cut through in correspondence with the impression which the wire has left in the mold with adhesive layer and support, the mold is provided with a perforation at each location where the wire is to be secured to the row of teeth, the shape and dimensions of this perforation determining the configuration of the point of attachment and said perforation having an open end on the side of the mold that does not come into contact with the row of teeth, and the wire is then re-positioned in the mold through the cut in the support.

6. A method according to claim 5, characterized in that applying the bonding agent is done via the open termination of a perforation after positioning the mold on the row of teeth and securing it temporarily by means of the adhesive layer.

7. A method according to claim 6, characterized in that starting from the side of the mold where the open termination is disposed, a channel is provided at a relatively short distance from said open termination, which channel terminates in the perforation and at least at that point has a relatively small passage compared with the perforation.

8. A method according to claim 7, characterized in that the channel has a frustoconical configuration, the narrowest passage of said channel being disposed at the termination in the perforation.

9. A method according to claim 1, characterized in that the adhesive layer is provided on the desired portions of the mold, for example by means of a "spray" method, after withdrawing the mold from the cast.

10. A method according to claim 9, characterized in that the aid is a wire, which is temporarily removed from the mold after withdrawal from the cast, the mold is provided with a perforation at each location where the wire is to be secured to the row of teeth, the form and dimensions of said perforation determining the configuration of the point of attachment and said perforation having an open termination on the side of the mold that does not come into contact with the row of teeth, the wire is re-positioned in its position in the mold, and then the adhesive layer is applied to the desired portions of the mold surface.

11. A method according to claim 10, characterized in that applying the bonding agent is done via the open termination of a perforation after position the mold on the row of teeth and temporarily securing it by means of the adhesive layer.

12. A method according to claim 11, characterized in that starting from the side of the mold where the open termination is disposed, a channel is provided at a relatively short distance from said open termination, said channel terminating in the perforation.

13. A method according to claim 12, characterized in that the channel has a frustoconical configuration, the narrowest passage of said channel being disposed at the termination in the perforation.

14. Apparatus for positioning an orthodontic aid to be secured with a bonding agent to a patient's tooth comprising: a mold of deformable material having an outer side and a first internal cavity conforming to a surface anatomy of corresponding portions of a patient's tooth, said mold further having second internal cavities communicating with said first internal cavity and adapted to receive the orthodontic aid, said first and second internal cavities having sides completely covered with an adhesive layer having a weaker adhesive strength than the bonding agent.

15. The apparatus of claim 14 wherein the adhesive layer is covered with a support, wherein the support can be removed so as to leave the adhesive layer on the mold.

16. The apparatus of claim 15 wherein the support is partly cut away to completely clear the sides of said second internal cavities from said support and each of said second cavities has a bracket situated in direct contact with the adhesive layer.

17. The apparatus of claim 15 wherein the orthodontic aid comprises a wire embedded in the mold, the support being cut through at places where said second internal cavities communicate with said first internal cavity, said places forming a line with a length equal to the length of the wire, the mold being provided with a number of perforations to be filled with the bonding agent, and said perforations extending between said first internal cavity and said outer side of the mold and clearing a part of the embedded wire.

18. The apparatus of claim 17 further comprising a channel extending from each perforation to the outer side of the mold.

* * * * *